United States Patent
Park

(10) Patent No.: US 11,723,849 B2
(45) Date of Patent: *Aug. 15, 2023

(54) HAIR CARE COMPOSITIONS

(71) Applicant: L'OREAL, Paris (FR)

(72) Inventor: Jung Hyun Park, Westfield, NJ (US)

(73) Assignee: L'OREAL, Paris (FR)

(*) Notice: Subject to any disclaimer, the term of this patent is extended or adjusted under 35 U.S.C. 154(b) by 205 days.

This patent is subject to a terminal disclaimer.

(21) Appl. No.: 17/218,438

(22) Filed: Mar. 31, 2021

(65) Prior Publication Data

US 2021/0299011 A1  Sep. 30, 2021

Related U.S. Application Data

(60) Provisional application No. 63/002,820, filed on Mar. 31, 2020.

(51) Int. Cl.
| | |
|---|---|
| *A61Q 5/06* | (2006.01) |
| *A61Q 5/12* | (2006.01) |
| *A61K 8/34* | (2006.01) |
| *A61K 8/37* | (2006.01) |
| *A61K 8/31* | (2006.01) |
| *A61K 8/42* | (2006.01) |
| *A61K 8/41* | (2006.01) |

(52) U.S. Cl.
CPC ............... *A61K 8/345* (2013.01); *A61K 8/31* (2013.01); *A61K 8/342* (2013.01); *A61K 8/37* (2013.01); *A61K 8/415* (2013.01); *A61K 8/42* (2013.01); *A61Q 5/06* (2013.01); *A61Q 5/12* (2013.01); *A61K 2800/262* (2013.01); *A61K 2800/34* (2013.01); *A61K 2800/48* (2013.01); *A61K 2800/596* (2013.01); *A61K 2800/805* (2013.01)

(58) Field of Classification Search
CPC ... A61Q 5/06; A61Q 5/12; A61Q 5/00; A61K 8/415; A61K 8/42; A61K 8/34; A61K 8/37; A61K 8/416; A61K 2800/262; A61K 2800/596

See application file for complete search history.

(56) References Cited

U.S. PATENT DOCUMENTS

| | | | |
|---|---|---|---|
| 8,563,016 B2 | 10/2013 | Agarelli et al. | |
| 2007/0166258 A1 | 7/2007 | Pratley et al. | |
| 2008/0279801 A1* | 11/2008 | Dickinson ............... | A61K 8/068 424/70.1 |
| 2017/0216172 A1 | 8/2017 | Carballad et al. | |
| 2020/0206111 A1 | 7/2020 | Lee et al. | |

FOREIGN PATENT DOCUMENTS

| | | |
|---|---|---|
| JP | 2016117715 A | 6/2016 |
| KR | 20080010846 A | 1/2008 |
| KR | 20130046109 A | 5/2013 |
| KR | 101309972 B1 | 9/2013 |
| KR | 20150111715 A | 10/2015 |
| WO | 03037280 A1 | 5/2003 |
| WO | 2006119042 A1 | 11/2006 |
| WO | WO-2018097303 A1 * | 5/2018 ............. A61K 8/068 |
| WO | 2019156484 A1 | 8/2019 |
| WO | 2020142514 A1 | 7/2020 |
| WO | 2020142521 A1 | 7/2020 |
| WO | 2020257889 A1 | 12/2020 |

OTHER PUBLICATIONS

Preliminary Search Report and Written Opinion dated Feb. 24, 2021 for corresponding French Application No. FR2006214.

* cited by examiner

*Primary Examiner* — Tracy Liu
*Assistant Examiner* — Lucy M Tien
(74) *Attorney, Agent, or Firm* — Polsinelli PC

(57) ABSTRACT

The present disclosure relates to hair care and conditioning compositions comprising polyols; monoalcohols having from 2 to 6 carbon atoms; fatty alcohols selected from cetyl alcohol and myristyl alcohol; cationic surfactants; fatty carbonate esters; and dialkyl ethers. When the composition is applied to the wet or damp hair or put in contact with extraneous water, the composition forms an emulsion having a lamellar phase. The present disclosure also relates to methods of treating hair using these compositions.

34 Claims, No Drawings

HAIR CARE COMPOSITIONS

CROSS-REFERENCE TO RELATED APPLICATIONS

This patent application claims benefit of priority to U.S. Patent Application Ser. No. 63/002,820, filed on Mar. 31, 2020, the disclosure of which is incorporated by reference as if fully rewritten herein.

FIELD OF THE DISCLOSURE

The present disclosure relates to hair care and treatment compositions and to methods for caring for and providing cosmetic benefits to the hair using the compositions.

BACKGROUND

Many individuals suffer from dry and damaged hair. Dryness and damage can occur due to several factors including weather exposure, mechanical treatments (e.g. brushing hair), excessive treatments using chemicals, dying hair, heat styling, etc. In combination, using cleansing products that can be excessively stripping of hair's natural oils, can also lead to split ends, dull hair, and exacerbate dry hair. To mitigate the damage, oil treatments, conditioner, hair masks, and chemical treatments are commonly used.

The popularity and usage of oils for dry hair treatments has increased due to their effectiveness and simplicity. Commonly used oils include olive oil, mineral oil, avocado oil, apricot kernel oil, rice bran oil, and coconut oil. However, one problem is that effects are not usually seen after more than several hours (e.g. 8 hours) of treatment and several treatments are usually required, making it time consuming and labor intensive.

Individuals desire a treatment for hair or damaged hair that is not time consuming and labor intensive to use. A variety of approaches have been developed to condition the hair. A common method of providing conditioning benefit is through the use of rinse-off and leave-on hair conditioners and masks containing conditioning agents such as cationic surfactants and polymers, high melting point fatty compounds, low melting point oils, silicone compounds, and mixtures thereof. Such products typically contain a substantial amount of water or are in the form of emulsions.

However, there could still be some drawbacks to conventional conditioner products such as being too heavy on the hair or weighing down the hair and/or being greasy. In addition, some products may not sufficiently condition or improve the sensorial feel of the hair or reduce the damaged feel of hair. Thus, there is still a need for providing hair care or hair treatment products which provide improved hair manageability, for example, improved hair alignment and reduced unwanted volume (especially reduced frizz), as well as hair repair benefits or less damaged feel to hair (especially for damaged hair), a weightless feel on hair (hair is not weighed down) and improved overall appearance of the hair. There is also a need to develop hair care products that can impart other benefits at the same time in addition to caring and conditioning benefits, such as improved shine, detangling, ease of combing, smoothness, shape, discipline, and sealed ends of the hair desirable volume, curl definition (for curly or wavy hair), and restylability or reshaping (without the need to reapply the product).

SUMMARY OF THE DISCLOSURE

The instant disclosure relates to hair care and treatment compositions; and to methods for conditioning and caring for the hair using the compositions. The compositions are transparent and are anhydrous or substantially anhydrous (i.e., the amount of water can be about 10 wt. % or less). Upon application to wet or damp hair, or when the composition is contacted with extraneous water, the composition forms an emulsion in a lamellar phase structure, which surprisingly enhances the delivery of conditioning active agents such as cationic surfactants, emollients, and fatty compounds onto a surface such as hair. The deposition of these conditioning active agents impart a smoothing and lubricating effect to the hair, resulting in the hair having a shiny and healthy appearance and tactile repairing sensation. The hair is easily detangled and dryness and frizziness are reduced or minimized. The compositions typically include:
  (a) about 20 wt. % or higher of one or more polyols;
  (b) about 5 to about 70 wt. % of one or more monoalcohols having from 2 to 6 carbon atoms;
  (c) about 2 wt. % or less of one or more fatty alcohols selected from cetyl alcohol and myristyl alcohol;
  (d) about 0.1 to about 5 wt. % of one or more cationic surfactants;
  (e) about 1 wt % or less of one or more fatty carbonate esters;
  (f) about 1 wt % or less of one or more dialkyl ethers; and
  (g) 0 wt. % to about 10 wt. % of water;
all percentages by weight are based on the total weight of the composition.

The composition of the present disclosure is transparent and is solubilized, non-emulsified until applied to wet or damp hair or put in contact with extraneous water, whereupon the composition forms an opaque emulsion. In an embodiment, the resulting opaque emulsion has a lamellar phase structure.

The compositions of the present disclosure can be applied immediately after shampooing the hair, for example, in place of a conditioner. The compositions can also be applied on hair immediately after shampooing and conditioning the hair, for example, as a rinse-off or leave-in treatment. The compositions can also be applied before shampooing the hair as pre-shampoo treatment compositions. The compositions can also be used on hair by themselves, without requiring the use of any other hair product. Moreover, the compositions are applied directly to wet or damp hair and massaged into the hair to ensure uniform coverage. The compositions can also first be combined with a small amount of extraneous water, with the resulting mixture being applied immediately onto hair and massaged into the hair to ensure uniform coverage. After application to the hair, the hair may be rinsed with water, dried, and styled as desired. Another unique aspect of the compositions is that they may be used as a leave-on product. The compositions can be applied to wet or damp hair or first mixed with a small amount of extraneous water, and allowed to remain on the hair indefinitely, i.e., the hair composition is not removed or rinsed from the hair prior to drying and/or shaping or styling the hair.

DETAILED DESCRIPTION OF THE DISCLOSURE

The present disclosure relates to a hair care composition comprising:
  (a) about 20 wt. % or higher of one or more polyols;
  (b) about 5 to about 70 wt. % of one or more monoalcohols having from 2 to 6 carbon atoms;
  (c) about 2 wt. % or less of one or more fatty alcohols selected from cetyl alcohol and myristyl alcohol;

(d) about 0.1 to about 5 wt. % of one or more cationic surfactants;

(e) about 1 wt % or less of one or more fatty carbonate esters;

(f) about 1 wt % or less of one or more dialkyl ethers; and (g) 0 wt. % to about 10 wt. % of water;

all percentages by weight are based on the total weight of the composition.

In an embodiment, the composition of the present disclosure is transparent and in solubilized, non-emulsified until applied to wet or damp hair or put in contact with extraneous water, whereupon the composition forms an opaque emulsion.

In an embodiment, the composition forms an emulsion that is a lamellar phase in situ when it comes in contact with water present on wet or damp hair.

In an embodiment, the weight ratio of the polyol(s) to the monoalcohols (polyols:monoalcohols) in the compositions of the present disclosure is from about 20:1 to about 1:1.

In an embodiment, the one or more polyol(s) is selected from ethylene glycol, propylene glycol, butylene glycol, hexylene glycol, pentylene glycol, diethylene glycol, dipropylene glycol, 1,3 propanediol, glycerin, or mixtures thereof.

In an embodiment, the one or more polyol(s) is not butylene glycol.

In an embodiment, the one or more monoalcohols is selected from ethanol, butanol, pentanol, hexanol, isopropyl alcohol, cycohexanol, isobutyl alcohol, 2-methyl-2-butanol (2-methylbutan-2-ol), and a mixture thereof.

In an embodiment, the one or more polyol(s) is selected from propylene glycol and the one or more monoalcohols is selected from ethanol wherein the weight ratio of propylene glycol to ethanol (propylene glycol:ethanol) is from about 15:1 to about 1:1 or from about 10:1 to about 1.5:1 or from about 8:1 to about 2:1 or from about 5:1 to about 2:1.

In an embodiment, the weight ratio of the one or more fatty alcohols to the one or more cationic surfactant (fatty alcohols:cationic surfactants) is from about 2:1 to about 1:1, about 2:1 to about 1.1:1, about 2:1 to about 1.2:1, about 2:1 to about 1.3:1, about 2:1 to about 1.4:1, about 2:1 to about 1.5:1, about 2:1 to about 1.6:1, or about 2:1 to about 1.7:1.

In an embodiment, the weight ratio of the one or more fatty carbonate esters to one or more dialkyl ethers (fatty carbonate esters:dialkyl ether) is from about 2:1 to 1:1, about 2:1 to 1.1:1, about 2:1 to 1.2:1, about 2:1 to 1.3:1, about 2:1 to 1.4:1, about 2:1 to 1.5:1, about 2:1 to 1.6:1, about 2:1 to 1:7:1, or about 2:1 to 1.8:1.

In an embodiment, the composition further comprises one or more isopropyl esters.

In an embodiment, the composition further comprises one or more additional esters other than isopropyl esters.

In an embodiment, the composition further comprises one or more isopropyl esters and one or more additional esters other than isopropyl esters.

The present disclosure also relates to methods of treating or caring for the hair comprising applying onto hair the hair care compositions of the present disclosure.

In various embodiments, the compositions of the present disclosure provide to hair one or more of improved shine, detangling, ease of combing, smoothness, sleekness, shape, discipline, sealed ends of the hair, desirable volume, weightless feel (does not weigh the hair down), and curl care and definition (for curly or wavy hair).

The term "transparent" with respect to a transparent composition indicates that the composition has transmittance of at least 80% at a wavelength of 600 nm, for example measured using a Lambda 40 UV-visible spectrometer. The compositions may have, for example, a transmittance of at least 80%, at least 90%, or at least 95% at a wavelength of 600 nm, measured, for example, using a Lambda 40 UV-visible spectrometer. The term "transparent" is interchangeable with the term "clear" for purposes of the instant disclosure. The term "transparent" can also mean that an article is visible to the human eye when looking through the composition contained in a clear glass bottle.

The compositions can be substantially anhydrous. The phrase "substantially anhydrous" is interchangeable with the phrase "essentially free of water" or "substantially free of water." A substantially anhydrous composition may include up to 10 wt. % of water regardless of whether the water is added to the composition or part of a raw material. Nonetheless, the substantially anhydrous composition may include less than 9 wt. %, less than 8 wt. %, less than 7 wt. %, less than 6 wt. %, less than 5 wt. %, less than 4 wt. %, less than 3 wt. %, less than 2 wt. %, less than 1 wt. %, or less than 0.5 wt. % of water.

The compositions can be anhydrous, that is, they do not contain water or are free of water (added water or part of a raw material).

The compositions of the instant disclosure typically have a viscosity at 25° C. of about 10 mPa·s to about 10,000 mPa·s or about 10 mPa·s to about 8,000 mPa·s, or about 10 mPa·s to about 6,000 mPa·s, or about 10 mPa·s to about 4,000 mPa·s, or about 10 mPa·s to about 2,000 mPa·s, or about 10 mPa·s to about 1,000 mPa·s, or about 10 mPa·s to about 800 mPa·s, or about 10 mPa·s to about 600 mPa·s, or about 10 mPa·s to about 500 mPa·s, or about 10 mPa·s to <500 mPa·s, including ranges and sub-ranges there between. The viscosity measurements can be carried out, for example, using a Broooksfield viscometer, Model RVT (Brookfield Engineering Laboratories, Inc.) at about 20 revolutions per minute (RPM), at ambient room temperature of about 20 to 25° C.; spindle sizes may be selected in accordance with the standard operating recommendations form the manufacturer, ranging from disk spindle No. 1 to No. 4.

In an embodiment, when combined with the extraneous water, the cosmetic composition forms an emulsion, which typically is opaque and has a viscosity that is greater than that of the solubilized, non-emulsified, transparent composition prior to combination with the extraneous water.

In an embodiment, when combined with the extraneous water, the cosmetic composition forms an emulsion, in situ (either on the hair or on skin or other parts of the body), which typically is opaque and has a viscosity that is greater than that of the solubilized, transparent composition prior to combination with the extraneous water.

Polyol(s)

The hair care compositions include one or more polyols, e.g., such as those chosen from ethylene glycol, propylene glycol, butylene glycol, hexylene glycol, pentylene glycol, diethylene glycol, dipropylene glycol, 1,3 propanediol, glycerin, diglycerin, and a mixture thereof. The amount of polyol(s) present in the hair care composition typically ranges from about 20 wt. % or higher, based on the total weight of the hair treatment composition. For example, the amount of polyol(s) in the hair care composition may be about 20 to about 95 wt. %, about 20 to about 85 wt. %, about 20 to about 80 wt. %, about 20 to about 75 wt. %, about 20 to about 70 wt. %, about 20 to about 65 wt. %, about 20 to about 60 wt. %, about 20 to about 55 wt. %, about 20 to about 50 wt. %, about 20 to about 45 wt. %, about 20 to about 40 wt. %, about 20 to about 35 wt. %, about 20 to about 30 wt. %; about 25 to about 88 wt. %, about 25 to about 85 wt. %, about 25 to about 80 wt. %, about 25 to about 75 wt. %, about 25 to about 70 wt. %, about 25 to about 65 wt. %, about 25 to about 60 wt. %, about 25 to about 55 wt. %, about 25 to about 50 wt. %, about 25 to about 45 wt. %, about 25 to about 40 wt. %, about 25 to about 35 wt. %; about 30 to about 85 wt. %, about 30 to about 80 wt. %, about 30 to about 75 wt. %, about 30 to about 70 wt. %, about 30 to about 65 wt. %, about 30 to about 60 wt. %, about 30 to about 55 wt. %, about 30 to about 50 wt. %, about 30 to about 45 wt. %, about 30 to about 40 wt. %; about 40 to about 87 wt. %, about 40 to about 85 wt. %, about 40 to about 80 wt. %, about 40 to about 75 wt. %, about 40 to about 70 wt. %, about 40 to about 65 wt. %, about 40 to about 60 wt. %, about 40 to about 55 wt. %, about 40 to about 50 wt. %; about 50 to about 87 wt. %, about 50 to about 85 wt. %, about 50 to about 80 wt. %, about 50 to about 75 wt. %, about 50 to about 70 wt. %, about 50 to about 65 wt. %, about 50 to about 60 wt. %; about 60 to about 87 wt. %, about 60 to about 85 wt. %, about 60 to about 80 wt. %, about 60 to about 75 wt. %, about 60 to about 70 wt. %; about 65 to about 87 wt. %, about 65 to about 85 wt. %, about 65 to about 80 wt. %, about 65 to about 75 wt. %; about 70 to about 87 wt. %, about 70 to about 85 wt. %, about 70 to about 75 wt. %, including all ranges and sub-ranges there between, based on the total weight of the hair care composition.

The term "polyol" should be understood as meaning, within the meaning of the present disclosure, an organic molecule comprising at least two free hydroxyl groups. The polyols of the hair care composition may be glycols or compounds with numerous hydroxyl groups. In some cases, the one or more polyols is/are selected from the group consisting of $C_2$-$C_{32}$ polyols. The one or more polyols may be liquid at ambient temperature (25° C.). The one or more polyols may have from 2 to 32 carbon atoms, from 3 to 16 carbon atoms, or from 3 to 12 carbon atoms.

Polyols that may be included in the hair care composition, in certain instances, include ethylene glycol, propylene glycol, butylene glycol, hexylene glycol, pentylene glycol, 1,3-propanediol, dipropylene glycol, caprylyl glycol, glycerin, diglycerin, diethylene glycol, and dipropylene glycol, and mixtures thereof. In some cases, the polyol is propylene glycol. In some further cases, the polyol is one or both of propylene glycol and butylene glycol. Additionally, in some cases, the hair care composition comprises at least propylene glycol, and optionally one or more polyols other than propylene glycol.

Non-limiting examples of polyols that may be included in the hair care composition include and/or may be chosen from alkanediols such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, dipropylene glycol mono-iso-propyl ether, sorbitol, sorbitan, triacetin, and a mixture thereof.

The one or more polyols may, optionally, be glycols or glycol ethers such as, e.g., monomethyl, monoethyl and monobutyl ethers of ethylene glycol, propylene glycol or ethers thereof such as, e.g., monomethyl ether of propylene glycol, butylene glycol, hexylene glycol, dipropylene glycol as well as alkyl ethers of diethylene glycol, e.g., monoethyl ether or monobutyl ether of diethylene glycol.

Monoalcohol(s)

The hair care compositions include monoalcohol(s), such as those having from 2 to 6 carbon atom. The amount of monoalcohol present in the hair treatment composition may range from about 5 to about 50 wt. %, based on the total weight of the hair treatment composition. For example, the hair care composition may have monoalcohol in an amount of about 5 to about 50 wt. %, about 5 to about 45 wt. %, about 5 to about 40 wt. %, about 5 to about 35 wt. %, about 5 to about 30 wt. %, about 5 to about 25 wt. %; about 10 to about 50 wt. %, about 10 to about 45 wt. %, about 10 to about 40 wt. %, about 10 to about 35 wt. %, about 10 to about 30 wt. %, about 10 to about 25 wt. %; about 15 to about 50 wt. %, about 15 to about 45 wt. %, about 15 to about 40 wt. %, about 15 to about 35 wt. %, about 15 to about 30 wt. %, or about 15 to about 25 wt. % including all ranges and sub-ranges there between, based on the total weight of the hair care composition.

The one or more monoalcohols of the hair care composition may be chosen from ethanol, propanol, butanol, pentanol, hexanol, isopropyl alcohol, cycohexanol, isobutyl alcohol, 2-methyl-2-butanol (2-methylbutan-2-ol), and a mixture thereof. In one instance, the one or more monoalcohol(s) includes or consists of ethanol.

The total amount of polyol(s) is typically at least the same or higher than the total amount of the monoalcohol(s) having from 2 to 6 carbon atoms in the compositions. Often, the compositions include more polyol(s) than monoalcohol(s) having from 2 to 6 carbon atoms, i.e., a higher weight percent of the composition is a polyol(s) than monoalcohols having from 2 to 6 carbon atoms. The ratio of polyol(s) to the total amount of monoalcohol(s) having from 2 to 6 carbon atoms (polyol(s):monoalcohol(s)) may be from 20:1 to 1:1. In some instances, the ratio is from 20:1 to 1.1:1, 20:1 to 1.5:1, or 20:1 to 2:1, including ranges and sub-ranges there between. Similarly, in some instances, the ratio is from about 18:1 to 1:1, about 18:1 to 1.1, about 18:1 to 1.5:1, about 18:1 to 2:1, about 15:1 to 2:1, about 12:1 to 2:1, about 10:1 to 2.5:1, about 8:1 to 2.5:1, about 5:1 to 2.5:1, or about 5:1 to 3:1, including ranges and sub-ranges there between.

Fatty Alcohol(s)

The total amount of the one or more fatty alcohols selected from cetyl alcohol and myristyl alcohol in the compositions may vary but is typically about 2 wt. % or less, such as from about 0.1 to about 2 wt. %, based on the total weight of the composition. The total amount of fatty alcohols selected from cetyl alcohol and myristyl alcohol may be from about 0.1 to about 1.9 wt. %, about 0.1 to about 1.8 wt. %, about 0.1 to about 1.7 wt. %, about 0.5 to about 1.7 wt. %, about 0.5 to about 1.6 wt. %, about 0.5 to about 1.5 wt. %, or about 0.5 to about 2 wt. %, about 0.6 to about 2 wt. %, about 0.8 to about 2 wt. %, about 0.9 to about 2 wt. %, about 1 to about 2 wt. %, about 1.1 to about 2 wt. %, about 1.2 to about 2 wt. %, about 1.4 to about 2 wt. %, or about 1.5 to about 2 wt. %, including ranges and sub-ranges there between, based on the total weight of the composition.

The term "fatty alcohol" means an alcohol comprising at least one hydroxyl group (OH), and comprising at least 8 carbon atoms, and which is neither oxyalkylenated (in particular neither oxyethylenated nor oxypropylenated) nor glycerolated. The fatty alcohols can be represented by: R—OH, wherein R denotes a saturated (alkyl) or unsaturated (alkenyl) group, linear or branched, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

In addition to the fatty alcohols selected from cetyl alcohol and myristyl alcohol, the compositions of the instant disclosure may optionally include one or more of additional fatty alcohols such as decyl alcohol, undecyl alcohol, dodecyl alcohol, cetearyl alcohol (mixture of cetyl alcohol and stearyl alcohol), stearyl alcohol, isostearyl alcohol, isocetyl alcohol, behenyl alcohol, linalool, oleyl alcohol, cis4-t-butylcyclohexanol, isotridecyl alcohol, myricyl alcohol and a mixture thereof.

Cationic Surfactant(s)

The term "cationic surfactant" means a surfactant that may be positively charged when it is contained in the compositions according to the disclosure. This surfactant may bear one or more positive permanent charges or may contain one or more functional groups that are cationizable in the composition according to the disclosure. Non-limiting examples of cationic surfactants include cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and mixtures thereof.

In some instances, the cationic surfactant is preferably selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and mixtures thereof.

In some instances, the cationic surfactants are more preferably selected from cetrimonium chloride, behentrimonium chloride, behentrimonium methosulfate, stearamidopropyl dimethylamine, and a mixture thereof.

Moreover, in some cases, the cationic surfactant is most preferably cetrimonium chloride, behentrimonium chloride, or a mixture thereof.

A more exhaustive list of cationic surfactants that may be included in the hair-treatment compositions is provided later, under the heading "Cationic Surfactants."

The total amount of cationic surfactant(s) in the composition can vary but is typically from about 0.1 to about 5 wt. %, based on the total weight of the composition. In some cases, the total amount of cationic surfactant(s) is from about 0.1 to about 4 wt. %, about 0.1 to about 3 wt. %, about 0.1 to about 2 wt. %, about 0.5 to about 5 wt. %, about 0.5 to about 4 wt. %, about 0.5 to about 3 wt. %, or about 0.5 to about 2 wt. %, including ranges and sub-ranges there between, based on the total weight of the composition.

The total amount of fatty alcohol(s) is typically at least the same or higher than the total amount of the cationic surfactants in the compositions. Often, the compositions include more fatty alcohols than cationic surfactants i.e., a higher weight percent of the composition is a fatty alcohol than cationic surfactants. The ratio of fatty alcohol(s) to the total amount of cationic surfactants (fatty alcohol(s):cationic surfactants) may be from about 2:1 to 1:1, about 2:1 to 1.1:1, about 2:1 to 1.2:1, about 2:1 to 1.3:1, about 2:1 to 1.4:1, about 2:1 to 1.5:1, about 2:1 to 1.6:1, or about 2:1 to 1.7:1, including ranges and sub-ranges there between.

Fatty Carbonate Ester(s)

The compositions of the instant disclosure include one or more fatty carbonate esters (also referred to as "fatty carbonates"). Fatty carbonate esters include dialkyl carbonates. Non-limiting examples of dialkyl carbonates include those of the following formula: $R_1O(C=O)R_2$, wherein $R_1$ and $R_2$ are independently linear or branched, saturated or unsaturated alkyl chains having 1 to 30 carbon atoms, or having 2 to 28 carbon atoms, or having 4 to 25 carbon atoms, or having 6 to 22 carbon atoms, for example, C14-15 dialkyl carbonate, dicaprylyl carbonate, diethyl carbonate, dihexyl carbonate, diethylhexyl carbonate, dimethoxyphenyl phenyloxoethyl ethylcarbonate, dimethyl carbonate, dipropyl carbonate, dipropylheptyl carbonate, dioctyl carbonate, and a mixture thereof. In some instances, it is preferable to include one or more dialkyl carbonates, in particular dicaprylyl carbonate. The total amount of the one or more fatty carbonate ester(s) in the composition can vary but is typically about 1 wt % or less, based on the total weight of the composition. In some cases, the total amount of fatty carbonate ester(s) is from about 0.05 to about 1 wt. %, about 0.07 to about 1 wt. %, about 0.08 to about 1 wt. %, about 0.1 to about 0.9 wt. %, about 0.2 to about 0.7 wt. %, about 0.3 to about 0.6 wt. %, or about 0.3 to about 0.5 wt. %, including ranges and sub-ranges there between, based on the total weight of the composition.

In certain embodiments, the total amount of the one or more fatty carbonate ester(s) in the composition is about 1 wt,%, 0.9 wt,%, 0.8 wt,%. 0.7 wt,%, 0.6 wt,%, 0.5 wt,%, 0.4 wt, %, 0.3 wt, %, 0.2 wt, %, 0.1 wt,%, 0.08 wt,%, 0.07 wt,%, 0.06 wt,%, 0.05 wt,%, 0.04 wt,%, 0.03 wt,%, 0.02 wt,%, or 0.01 wt,%, based on the total weight of the composition.

Dialkyl Ether(s)

The compositions of the instant disclosure include one or more dialkyl ethers. Non-limiting examples of dialkyl ethers include dicaprylyl ether, dicetyl ether, dodecyl ether, dilauryl ether, dimyristyl ether, distearyl ether, diisononyl ether, and a mixture thereof.

The total amount of the one or more dialkyl ether(s) in the composition can vary but is typically about 1 wt % or less, based on the total weight of the composition. In some cases, the total amount of dialkyl ether(s) is from about 0.05 to about 1 wt. %, about 0.07 to about 1 wt. %, about 0.08 to about 1 wt. %, about 0.1 to about 0.9 wt. %, about 0.2 to about 0.7 wt. %, about 0.3 to about 0.6 wt. %, or about 0.3 to about 0.5 wt. %, including ranges and sub-ranges there between, based on the total weight of the composition.

In certain embodiments, the total amount of the one or dialkyl ether(s)) in the composition is about 1 wt,%, 0.9 wt,%, 0.8 wt,%. 0.7 wt,%, 0.6 wt,%, 0.5 wt,%, 0.4 wt,%, 0.3 wt,%, 0.2 wt,%, 0.1 wt,%, 0.08 wt,%, 0.07 wt,%, 0.06 wt,%, 0.05 wt,%, 0.04 wt,%, 0.03 wt,%, 0.02 wt,%, or 0.01 wt,%, based on the total weight of the composition.

The total amount of fatty carbonate ester(s) is typically at least the same or higher than the total amount of the dialkyl ether(s) in the compositions. The compositions may include more fatty carbonate ester(s) than dialkyl ether(s), i.e., a higher weight percent of the composition is a fatty carbonate ester(s) than dialkyl ether(s). The ratio of fatty carbonate ester(s) to the total amount of dialkyl ether(s) (fatty carbonate ester(s):dialkyl ether(s)) may be from about 2:1 to 1:1, about 2:1 to 1.1:1, about 2:1 to 1.2:1, about 2:1 to 1.3:1, about 2:1 to 1.4:1, about 2:1 to 1.5:1, about 2:1 to 1.6:1, about 2:1 to 1:7:1, or about 2:1 to 1.8:1, including ranges and sub-ranges there between.

Water

The hair care compositions may be devoid of added water, i.e., the compositions do not contain water that is added to the composition or present in a raw material.

The hair care composition can comprise from 0 up to about 10 wt. % of water. For example, the amount of water present in the composition prior to combination with extraneous water may be from about 0.01 to about 10 wt. % or about 0.05 to about 9 wt. %, or about 0.1 to about 8 wt. % or about 0.2 to about 7 wt. % or about 0.3 to about 6 wt. % or about 0.5 to about 5 wt. % or about 0.6 to about 4 wt. % or about 0.7 to about 3 wt. % or about 0.5 to about 2 wt. % or about 0.5 to about 1 wt. % or less than 2 wt. %, or less than 1 wt. %, or less than 0.5 wt. % or less than 0.3 wt. %, including ranges and sub-ranges there between, based on the total weight of the hair care composition. In some instances, the water present in the hair care composition prior to combination with extraneous water is added to the composition ("added water"). In some instances, the water present in the cosmetic composition prior to combination with extraneous water is not "added water," i.e., it is present in the hair care composition as part of a raw material that is included in the composition. Although the hair care composition may include water prior to the combination of extraneous water, in some embodiments the hair care composition is anhydrous or devoid of water.

Esters

The compositions of the instant disclosure may optionally include an isopropyl ester. More specific non-limiting examples include isopropyl isostearate, isopropyl myristate, isopropyl palmitate, diisopropyl sebacate, diisopropyl dimer dilinoleate, and mixtures thereof.

The compositions of the instant disclosure may also optionally include one or more of additional esters other than isopropyl esters. Non-limiting examples of the additional esters other isopropyl esters include glycerol fatty esters, sucrose fatty esters, sorbitan fatty ester, fatty acid esters, or mixtures thereof. Additional non-limiting examples are esters of C6-22 fatty acids with a monohydric alcohol and/or esters of C6-22 fatty alcohols with a mono-carboxylic acid. More specific non-limiting examples include n-propyl myristate, hexyl laurate, hexadecyl isostearate, hexydecyl laurate, hexyldecyl octanoate, n-propyl palmitate, and mixtures thereof.

In some cases, the one or more additional esters is a glycerol ester of fatty acids or glyceryl esters (or glycerol fatty esters), for example, glyceryl monomyristate, glyceryl monopalmitate, glyceryl monostearate, glyceryl isostearate, glyceryl monooleate, glyceryl dioleate, glyceryl distearate, glyceryl laurate, trilaurin, triarachidin, tribehenin, tricaprin, tricaprylin, caprylic/capric triglyceride, trierucin, triheptanoin, triheptylundecanoin, triisononanoin, triisopalmitin, triisostearin, trilinolein, trimyristin, trioctanoin, triolein, tripalmitin, tripalmitolein, triricinolein, tristearin, triundecanoin, and mixtures thereof.

Additional, non-limiting examples of additional esters include diisobutyl adipate, 2-hexyldecyl adipate, di-2-heptylundecyl adipate, monoisostearic acid N-alkyl glycol, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, isocetyl stearate, butyl stearate, diisopropyl sebacate, di-2-ethylhexyl sebacate, cetyl lactate, myristyl lactate, isopropyl palm itate, 2-ethylhexyl palm itate, 2-hexyldecyl palm itate, 2-heptylundecyl palm itate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, diisostearyl malate, and mixtures thereof.

In some instances, the additional esters are selected from sucrose fatty esters. A non-limiting but preferred example is sucrose palmitate. Additional examples include sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palmitate/stearate.

In certain embodiments, the one or more additional esters other than isopropyl esters include Ethylhexyl Palmitate, Ethylhexyl Stearate, Hexyl Laurate, Coco-Caprylate/Caprate, Cetearyl Ethylhexanoate, Propylene Glycol Dicaprylate/Dicaprate, and mixtures thereof.

The total amount of estersin the composition, if present, may vary but is typically from about 0.1 to about 2 wt. %, based on the total weight of the composition. In some instances, the total amount of esters is from about 0.1 to about 2 wt. %, about 0.1 to about 1.8 wt. %, about 0.1 to about 1.6 wt. %, about 0.1 to about 1.5 wt. %, about 0.2 to about 1.5 wt. %, about 0.3 to about 1.2 wt. %, about 0.4 to about 1 wt. %, about 0.4 to about 0.8 wt. %, or about 0.5 to about 0.7 wt. %, including ranges and sub-ranges there between, based on the total weight of the composition.

Alkanes

One or more alkanes such as undecane, tridecane or a mixture thereof can be included in the compositions of the instant disclosure.

The total amount of the one or more alkanes, if present, may vary but is typically from about 0.1 to about 10 wt. %, based on the total weight of the composition. In some instances, the total amount of the one or more alkanes is from about 0.1 to about 9 wt. %, about 0.1 to about 8 wt. %, about 0.1 to about 6 wt. %, about 0.1 to about 5 wt. %, about 0.2 to about 4 wt. %, about 0.3 to about 3 wt. %, about 0.4 to about 2 wt. %, about 0.4 to about 1.5 wt. %, or about 0.4 to about 1 wt. %, including ranges and sub-ranges therebetween, based on the total weight of the composition.

Other Optional Ingredients

One or more thickening agents can optionally be included in the compositions of the instant disclosure. Thickening agents may be referred to as "thickeners" or "viscosity modifying agents." Thickening agents are typically included to increase the viscosity of the compositions. Nonetheless, in some instances, certain thickening agents provide additional, surprising benefits to the compositions. Non-limiting examples of thickening agents include polyacrylate crosspolymers or crosslinked polyacrylate polymers, cationic acrylate copolymers, anionic acrylic or carboxylic acid polymers, polyacrylamide polymers, polysaccharides such as cellulose derivatives, gums, polyquaterniums, vinylpyrrolidone homopolymers/copolymers, C8-24 hydroxyl substituted aliphatic acid, C8-24 conjugated aliphatic acid, sugar fatty esters, polyglyceryl esters, and a mixture thereof. Particular types of thickening agents that may be mentioned include the following:

a. Carboxylic acid or carboxylate based homopolymer or co-polymer, which can be linear or crosslinked: These polymers contain one or more monomers derived from acrylic acid, substituted acrylic acids, and salts and esters of these acrylic acids (acrylates) and the substituted acrylic acids. Commercially available polymers include those sold under the trade names CARBOPOL, ACRYSOL, POLYGEL, SOKALAN, CARBOPOL ULTREZ, and POLYGEL. Examples of commercially available carboxylic acid polymers include the carbomers, which are homopolymers of acrylic acid crosslinked with allyl ethers of sucrose or pentaerytritol. The carbomers are available as the CARBOPOL 900 series from B.F. Goodrich (e.g., CARBOPOL 954). In addition, other suitable carboxylic acid polymeric agents include ULTREZ 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as CARBOPOL 1342, CARBOPOL 1382, PEMULEN TR-1, and PEMULEN TR-2, from B.F. Goodrich.

Other suitable carboxylic acid or carboxylate polymeric agents include copolymers of acrylic acid and alkyl C5-C10 acrylate, copolymers of acrylic acid and maleic anhydride, and polyacrylate crosspolymer-6. Polyacrylate Crosspolymer-6 is available in the raw material known as SEPIMAX ZEN from Seppic.

Another suitable carboxylic acid or carboxylate polymeric agent includes acrylamidopropyltrimonium chloride/acrylates copolymer, a cationic acrylates copolymer (or a quaternary ammonium compound), available as a raw material known under the tradename of SIMULQUAT HC 305 from Seppic.

In certain embodiments, the carboxylic acid or carboxylate polymer thickeners useful herein are those selected from carbomers, acrylates/C10-C30 alkyl acrylate crosspolymers, polyacrylate crosspolymer-6, acrylamidopropyltrimonium chloride/acrylates copolymer, and mixtures thereof.

b. Polyquaternium Compounds: Non-limiting examples, include polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-21, polyquaternium-22, polyquaternium-23, polyquaternium-24, polyquaternium-25, polyquaternium-26, polyquaternium-27, polyquaternium-28, polyquaternium-29, polyquaternium-30, polyquaternium-40, polyquaternium-41, polyquaternium-42, polyquaternium-43, polyquaternium-44, polyquaternium-45, polyquaternium-46, polyquaternium-47, polyquaternium-48, polyquaternium-49, polyquaternium-50, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-62, polyquaternium-63, polyquaternium-64, polyquaternium-65, polyquaternium-66, polyquaternium-67, etc. In some cases, preferred polyquaternium compounds include polyquaternium-10, polyquaternium-11, polyquaternium-67, and a mixture thereof.

c. Celluloses: Non-limiting examples of celluloses include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. In some instances, the cellulose is selected from water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt). Furthermore, in some instance, the cellulose is preferably hydroxypropylcellulose (HPC).

d. Polyvinylpyrrolidone (PVP) and co-polymers: Non-limiting examples include Polyvinylpyrrolidone (PVP), Polyvinylpyrrolidone (PVP)/vinyl acetate copolymer (PVP/VA copolymer), polyvinylpyrrolidone (PVP)/eicosene copolymer, PVP/hexadecene copolymer, etc. Commercially available polyvinylpyrrolidone includes LUVISKOL K30, K85, K90 available from BASF. Commercially available copolymers of vinylpyrrolidone and vinylacetate include LUVISKOL VA37, VA64 available from BASF; copolymers of vinylpyrrolidone, methacrylamide, and vinylimidazole (INCI: VP/Methacrylamide/Vinyl Imidazole Copolymer) is commercially available as LUVISET from BASF. In some instances, PVP and PVP/VA copolymer are preferred.

e. Sucrose esters: Non-limiting examples include sucrose palmitate, sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palmitate/stearate, and mixtures thereof.

f. Polyglyceryl esters: Non-limiting polyglycerol esters of fatty acids (polygylceryl esters) include those of the following formula:

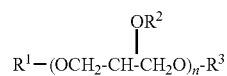

wherein n is from 2 to 20 or from 2 to 10 or from 2 to 5, or is 2, 3, 4, 5, 6, 7, 8, 9, or 10, and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.

g. C8-24 hydroxyl substituted aliphatic acid and C8-24 conjugated aliphatic acid: Non-limiting examples include conjugated linoleic acid, cis-parinaric acid, trans-7-octadecenoic acid, cis-5,8,11,14,17-eicosapentanoic acid, cis-4,7,10,13,16,19-docosahexenoic acid, columbinic acid, linolenelaidic acid, ricinolaidic acid, stearidonic acid, 2-hydroxystearic acid, alpha-linolenic acid, arachidonic acid, cis-11,14-eicosadienoic acid, linolelaidic acid, monopetroselinic acid, petroselinic acid, ricinoleic acid, trans-vaccenic acid, cis-11,14,17-eicosatrienoic acid, cis-5-eicosenoic acid, cis-8,11,14-eicosatrienoic acid, hexadecatrienoic acid, palmitoleic acid, petroselaidic acid, trans trans farnesol, cis-13,16-docosadienoic acid, cis-vaccenic acid, cis-11-eicosenoic acid, cis-13,16,19-docosatrienoic acid, cis-13-octadecenoic acid, cis-15-octadecanoic acid, cis-7,10,13,16 docosatetraenoic acid, elaidic acid, gamma-linolenic acid, geranic acid, geranyl geranoic acid, linoleic acid, oleic acid, pinolenic acid, trans-13-octadecenoic acid. More preferably, the aliphatic acid comprises 12-hydroxystearic acid, conjugated linoleic acid, or a mixture thereof.

h. Gums: Non-limiting examples of gums include gum arabic, tragacanth gum, karaya gum, guar gum, gellan gum, tara gum, locust bean gum, tamarind gum, xanthan gum, locust bean gum, Seneca gum, sclerotium gum, gellan gum, etc.

The total amount of thickening agents can vary but is typically from about 0.01 to about 20 wt. %, based on the total weight of the composition. In some instances, the total amount of thickening agents is about 0.01 to about 15 wt. %, about 0.01 to about 10 wt. %, about 0.01 to about 0.01 to about 8 wt. %, about 0.01 to about 6 wt. %, about 0.01 to about 5 wt. %, about 0.1 to about 20 wt. %, about 0.1 to about 15 wt. %, about 0.1 to about 10 wt. %, about 0.1 to about 8 wt. %, about 0.1 to about 6 wt. %, or about 0.1 to about 5 wt. %, including ranges and sub-ranges there between, based on the total weight of the composition.

In some instances, the compositions include one or more polyacrylate crosspolymers, for example, polyacrylate crosspolymer-6. The total amount of the polyacrylate crosspolymer(s) can vary but may be from about 0.01 to about 10 wt. %, based on the total weight of the compositions. In some instances, the total amount of polyacrylate crosspolymers is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, including ranges and sub-ranges there between, based on the total weight of the composition.

In some instances, the compositions include one or more carbomers, which are polymeric materials composed of acrylic acid monomers. The total amount of carbomers may vary but may be from about 0.01 to about 10 wt. %, based on the total weight of the compositions. In some instances, the total amount of carbomers is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, including ranges and sub-ranges there between, based on the total weight of the composition.

In some instances, the compositions include acrylamidopropyltrimonium chloride/acrylates copolymer, which is a copolymer of one or more of the monomers formed from the amide of acrylic acid, methacrylic acid and aminopropyltrimethyl-ammonium chloride and one or more monomers of acrylic acid, methacrylic acid or one of their esters. The total amount of acrylamidopropyltrimonium chloride/acrylates copolymer may vary but may be from about 0.01 to about 10 wt. %, based on the total weight of the compositions. In some instances, the total amount of acrylamidopropyltrimonium chloride/acrylates copolymer is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, including ranges and sub-ranges there between, based on the total weight of the composition.

In some instances, the compositions include one or more polyquaternium compounds. Non-limiting examples include polyquaternium-10, polyquaternium-11, and polyquaternium-67. The total amount of polyquaternium compounds may vary but may be from about 0.01 to about 10 wt. %, based on the total weight of the compositions. In some instances, the total amount of polyquaternium compounds is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, including ranges and sub-ranges there between, based on the total weight of the composition.

In some instances, the compositions include one or more cellulose thickeners (e.g., microcrystalline cellulose, carboxymethylcellulose, hydroxymethylcellulose, and hydroxypropylcellulose). The total amount of cellulose thickeners can vary but may be from about 0.01 to about 10 wt. %, based on the total weight of the compositions. In some instances, the total amount of cellulose thickeners is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, including ranges and sub-ranges there between, based on the total weight of the composition.

In some instances, the compositions include polyvinylpyrrolidone (PVP) and/or polyvinylpyrrolidone/vinyl acetate (VP/VA) copolymer. The total amount of PVP and/or VP/VA copolymer can vary but may be from about 0.01 to about 10 wt. %, based on the total weight of the compositions. In some instances, the total amount of PVP and/or VP/VA copolymer is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, including ranges and sub-ranges there between, based on the total weight of the composition.

In some cases, the compositions are free or essentially free of silicones. For example, the compositions include less than about 3 wt. %, 2 wt. %, 1 wt. %, or 0.5 wt. % of silicones, or preferably, do not contain silicones. In some cases, the compositions comprise silicones. Non-limiting examples of silicones include amine-functionalized silicones (e.g., amodimethicone), dimethicone, bis-aminopropyl dimethicone, trimethyl silylamodimethicon, etc.

Methods of Treating Hair

The compositions of the instant disclosure are useful for conditioning and/or managing the hair. When the compositions are applied to wet or damp hair they form a lamellar phase in situ. A "lamellar phase" refers generally to packing of polar-headed long chain nonpolar-tail molecules in an environment of bulk polar liquid (i.e., water from the hair), as sheets of bilayers separated by bulk liquid. The compositions can be applied to the wet or damp hair and may be massaged into the hair, for example, with the hands, and/or spread throughout the hair with a comb or brush. This results in a smoothing and softening of the hair, which reduces frizz, dryness, and unwanted volume, and increases shine. The compositions can remain in the hair or can optionally be rinsed from the hair prior to drying and/or styling of the hair.

Another unique aspect of the compositions is that they may be used as a leave-on product. The compositions can be applied to wet or damp hair and allowed to remain on the hair indefinitely, i.e., the hair composition is not removed or rinsed from the hair prior to styling the hair.

The methods of treating hair according to the disclosure also include methods according to various routines. For instance, the compositions may be mixed with a shampoo (or conditioner) prior to application to the hair. Alternatively, the composition may be layered on top of (or lathered into) hair to which the shampoo (or conditioner) is already applied. Furthermore, the composition may be applied separate from the shampoo (or conditioner), i.e., applied to the hair after the shampoo (or conditioner) has been rinsed from the hair.

The compositions of the instant disclosure may be incorporated into a kit. For example, the kits may include at least one composition according to the instant disclosure and one or more additional compositions, for example, a shampoo, a conditioner, etc. The various compositions are separately contained in the kits. In some instances, the kits include one or more compositions according the instant disclosure, a shampoo, and/or a conditioner, all of which are separately contained. The kits may also include one or more compositions according the instant disclosure, a shampoo, and a conditioner. Instructions, mixing components, brushes, gloves, measuring tools, etc., may also optionally be included in the kits.

The compositions may be packaged in a variety of different containers, such as, for example, a ready-to-use container. Non-limiting examples of useful packaging include tubes, jars, caps, unit dose packages, and bottles, including squeezable tubes and bottles. The packaging may be configured so that it can be attached to a wall, such as a wall in a bathroom, including walls of a shower or tub. For example, the packaging can be a container that is configured to attach to a wall, such that when pressure is applied to the container, the composition contained therein is expelled from one or more openings in the container. In some cases, the packaging is a tube, such as a tube with two compartments, or dual tubes, each forming a separate compartment. Each compartment may include a different composition. For example, one tube or compartment may include a composition according to the instant disclosure, and the other tube may include a composition to be used with the composition, for example, a shampoo, a conditioner, an all-in-one shampoo/conditioner (i.e., a conditioning shampoo; also referred to as a "co-wash").

Methods of treating hair according to the disclosure may vary but typically include applying a composition of the instant disclosure to the hair, allowing the composition to remain on the hair for a sufficient amount of time, and rinsing the compositions from the hair. The composition may be applied to the hair in a sequence with other compositions. For example, the compositions may be applied to the hair before shampooing the hair, after shampooing the hair, before conditioning the hair, and/or after conditioning the hair. The compositions, however, are not required to be used in a sequence.

In some cases, the compositions are used in conjunction with additional hair-treatment compositions in a routine, for example, during an individual's normal showering/bathing routine. The composition may be applied to the hair individually or may be combined with one or more additional compositions. Combining the compositions with one or more additional compositions (e.g., a shampoo, a conditioner, a rinse, etc.) can be useful for eliminating multiple steps from a routine. For instance, the composition may be mixed with a shampoo (or conditioner) prior to application to the hair. In this case, the mixture of the shampoo (or conditioner) and the composition are simultaneously applied to the hair during the cleansing or conditioning process and simultaneously rinsed from the hair. Alternatively, the composition may be layered on top of (or lathered into) hair to which a shampoo (or conditioner) has already been applied or vice versa. In this case, the composition may be applied to the hair and without rinsing it from the hair, a shampoo (or conditioner) is then subsequently applied to the hair. Alternatively, the shampoo (or conditioner) may be first applied to the hair and without rinsing the shampoo (or conditioner) from the hair, the hair-treatment composition is also applied to the hair.

When used in conjunction with a shampoo and/or a conditioner, the composition may be mixed or used with the shampoo and/or conditioner in a ratio of about 1:10 to about 10:1, about 1:5 to about 5:1, about 1:3 to about 3:1, about 1:2 to about 2:1, about 1:1 to about 4:1, about 1:1 to about 3:1, or about 1:1 to about 2:1 (hair-treatment composition of the instant disclosure: shampoo/conditioner, etc.).

The compositions of the instant disclosure may be allowed to remain on the hair for a minimum amount of time before being rinsed from the hair, but it is not necessary to allow the composition to remain on the hair for an extended period of time. Conveniently, the compositions can be applied and allowed to remain on the hair for a period of time that is typical for regular shampooing and/or conditioning. For example, the composition (whether combined with another hair-treatment composition such as a shampoo or conditioner) may be applied to the hair and allowed to remain on the hair for a few seconds (1, 2, 3, or 5 seconds) up to about 1, about 2, about 5, about 10, about 15, about 20, about 25, or about 30 minutes.

When the composition is not being mixed with another composition prior to application to the hair, the composition may be applied to the hair immediately after or before the hair it treated with another composition (e.g., a shampoo and/or a conditioner). For example, the hair-treatment compositions may be applied to the hair within about 1, 2, 5, 10, or 20 minutes before or after a shampoo and/or a conditioner is applied to the hair.

In various embodiments, the compositions of the present disclosure can be
- mixed with a shampoo prior to application to hair; or
- layered onto hair with a shampoo; or
- applied to hair after a shampoo has been rinsed from the hair; or
- layered onto hair with a conditioner; or
- mixed with a conditioner prior to application to hair; or
- applied to hair after a conditioner has been rinsed from the hair.

The compositions of the instant disclosure are unique in their ability to provide hair with improved manageability, long-lasting style and frizz control, and smoothness. Accordingly, the instant disclosure relates to methods for treating hair, for example, for improving the manageability of hair, for imparting lasting style and frizz control, and for imparting smoothness. More specifically, the compositions may be used in methods for conditioning the hair, providing curl definition to the hair, providing frizz control to the hair, improving ease of compatibility and detangling, and providing smoothness.

Embodiments

In certain embodiments, the compositions of the instant disclosure are transparent and substantially anhydrous cosmetic composition comprising:
(a) about 50 to about 80 wt. %, or about 60 to about 80 wt. %, or about 70 to about 80 wt. %, including ranges and sub-ranges there between, of one or more polyols, preferably selected from ethanol, butanol, pentanol, hexanol, isopropyl alcohol, cycohexanol, isobutyl alcohol, 2-methyl-2-butanol (2-methylbutan-2-ol), and a mixture thereof;
(b) about 10 to about 40 wt. %, or about 10 to about 35 wt. %, or about 10 to about 30 wt. %, including ranges and sub-ranges there between, of one or more monoalcohols having from 2 to 6 carbon atoms, preferably selected from ethanol, butanol, pentanol, hexanol, isopropyl alcohol, cycohexanol, isobutyl alcohol, 2-methyl-2-butanol (2-methylbutan-2-ol), and a mixture thereof;
wherein preferably, the weight ratio of the polyol(s) to the monoalcohols (polyols:monoalcohols) is from about 15:1 to 2:1, about 12:1 to 2:1, about 10:1 to 2.5:1, about 8:1 to 2.5:1, about 5:1 to 2.5:1, or about 5:1 to 3:1, including ranges and sub-ranges there between;
(c) about 1.2 to about 2 wt. %, or about 1.4 to about 2 wt. %, or about 1.5 to about 2 wt. %, including ranges and sub-ranges there between, of one or more fatty alcohols selected from cetyl alcohol and myristyl alcohol;
(d) about 0.5 to about 4 wt. %, about 0.5 to about 3 wt. %, or about 0.5 to about 2 wt. %, including ranges and sub-ranges there between, of one or more cationic surfactants selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof; wherein preferably, the weight ratio of the one or more fatty alcohols to the one or more cationic surfactant (fatty alcohols:cationic surfactants) is from about 2:1 to about 1:1;
(e) about 1 wt % or less of one or more fatty carbonate esters, preferably selected from C14-15 dialkyl carbonate, dicaprylyl carbonate, diethyl carbonate, dihexyl carbonate, diethylhexyl carbonate, dimethoxyphenyl phenyloxoethyl ethylcarbonate, dimethyl carbonate, dipropyl carbonate, dipropylheptyl carbonate, dioctyl carbonate, and a mixture thereof;
(f) about 1 wt % or less of one or more dialkyl ethers preferably selected from dicaprylyl ether, dicetyl ether, dodecyl ether, dilauryl ether, dimyristyl ether, distearyl ether, diisononyl ether, and a mixture thereof;
wherein preferably, the weight ratio of the one or more fatty carbonate esters to one or more dialkyl ethers (fatty carbonate esters:dialkyl ether) is from about 2:1 to 1:1; and
(g) 0 wt. % to about 10 wt. % of water;
(h) optionally, one or more esters comprising one or more isopropyl ester, one or more additional esters other than isopropyl ester, and a mixture thereof;
wherein the composition is a transparent and non-emulsified composition until applied to the wet or damp hair or put in contact with extraneous water, whereupon the composition forms an opaque emulsion which in one embodiment, is in lamellar phase; and
all percentages by weight are based on the total weight of the composition.

In certain embodiments, the instant disclosure is directed to methods of treating hair comprising applying the hair care compositions to wet or damp hair and forming opaque emulsion in situ.

In certain embodiments, the instant disclosure is directed to methods of treating hair comprising: (i) putting the transparent compositions in contact with an amount of extraneous water such that an opaque emulsion in lamellar phase is formed; and (ii) applying the resulting mixture onto hair.

Implementation of the present disclosure is provided by way of the following examples. The examples serve to illustrate the technology without being limiting in nature.

Example 1

(Invention Compositions)

| | Ingredient INCI US NAME | FORMULA A wt. % | B wt. % | C wt. % | D wt. % | E wt. % | F wt. % |
|---|---|---|---|---|---|---|---|
| Glycol | PROPYLENE GLYCOL | qs to 100 (73.6-75.6) | qs to 100 (73.6-75.6) | qs to 100 (73.6-75.6) | qs to 100 (73.4-75.4) | qs to 100 (72.7-74.7) | qs to 100 (73.5-75.5) |
| Monoalcohol | ETHANOL | 20 | 20 | 20 | 20 | 20 | 20 |
| Fatty Alcohol | CETYL ALCOHOL | 2.0 | 2.0 | 1.5 | 1.5 | 1.5 | 1.5 |
| Cationic Surfactant | STEARAMIDOPROPYL DIMETHYLAMINE | 1.0 | 1.0 | 1.0 | 1.2 | 1.5 | 1.2 |
| Fatty Carbonate Ester | DICAPRYLYL CARBONATE | 0.9 | 0.7 | 0.9 | 0.9 | 0.9 | 0.9 |
| Dialkyl ether | DICAPRYLYL ETHER | 0.5 | 0.7 | 0.5 | 0.5 | 0.5 | 0.9 |
| Isopropyl ester | ISOPROPYL MYRISTATE | — | — | 0.5 | 0.5 | 0.9 | — |
| Misc. | ONE OR MORE OF PRESERVATIVES, FRAGRANCE, SALTS, pH ADJUSTERS, NONIONIC SURFACTANTS, ETC. | ≤2 | ≤2 | ≤2 | ≤2 | ≤2 | <2 |
| | RATIOS | | | | | | |
| | fatty carbonate ester:dialkyl ether | 1.8 | 1 | 1.8 | 1.8 | 1.8 | 1 |
| | fatty alcohol:cationic surfactant | 2 | 2 | 1.5 | 1.25 | 1. | 1.25 |
| | glycol:monoalcohol | 3.7 | 3.7 | 3.7 | 3.7 | 3.7 | 3.7 |
| | fatty carbonate ester:dialkyl ether:isopropyl ester | — | — | 2:1:1 | 2:1:1 | 1.8:1:1.8 | — |

Example 2

(Invention Compositions)

| | INGREDIENT INCI US NAME | FORMULA G wt. % | H wt. % | I wt. % | J wt. % |
|---|---|---|---|---|---|
| Glycol | PROPYLENE GLYCOL | qs to 100 (73.3-75.3) | qs to 100 (72.4-74.4) | qs to 100 (72.8-74.8) | qs to 100 (73.3-75.3) |
| Monoalcohol | ETHANOL | 20 | 20 | 20 | 20 |
| | ISOPROPYL ALCOHOL | 0.14 | 0.3 | 0.3 | 0.3 |
| Fatty Alcohol | CETYL ALCOHOL | 1.5 | 1.5 | 1.5 | 1.5 |
| Cationic Surfactant | BEHENTRIMONIUM CHLORIDE | 0.6 | 1.5 | 1.3 | 1.5 |
| | CETRIMONIUM CHLORIDE | 0.6 | — | — | — |
| Fatty Carbonate Ester | DICAPRYLYL CARBONATE | 0.9 | 0.9 | 0.9 | 0.9 |
| Dialkyl ether | DICAPRYLYL ETHER | 0.5 | 0.5 | 0.5 | 0.5 |
| Isopropyl ester | ISOPROPYL MYRISTATE | 0.5 | 0.9 | 0.5 | 0.5 |
| Misc. | ONE OR MORE OF PRESERVATIVES, FRAGRANCE, SALTS, pH ADJUSTERS, NONIONIC SURFACTANTS, ETC. | ≤2 | ≤2 | ≤2 | ≤2 |

-continued (Invention Compositions)

| INGREDIENT INCI US NAME | FORMULA G wt. % | H wt. % | I wt. % | J wt. % |
|---|---|---|---|---|
| WATER | ≤2 | ≤2 | ≤2 | ≤2 |
| RATIOS | | | | |
| fatty carbonate ester: dialkyl ether | 1.8 | 1.8 | 1.8 | 1.8 |
| fatty alcohol: cationic surfactant | 1.25 | 1 | 1.2 | 1 |
| glycol: monoalcohol | 3.6 | 3.7 | 3.7 | 3.7 |
| fatty carbonate ester: dialkyl ether: isopropyl ester | — | 1.8:1:1.8 | — | — |

Example 3

(Invention Compositions)

| | INGREDIENT INCI US NAME | K wt. % | L wt. % | M wt. % | N wt. % |
|---|---|---|---|---|---|
| Glycol | PROPYLENE GLYCOL | qs to 100 (73.3-75.3) | qs to 100 (73-75) | qs to 100 (73.4-75.4) | qs to 100 (73.8-75.8) |
| Monoalcohol | ETHANOL | 20 | 20 | 20 | 20 |
| | ISOPROPYL ALCOHOL | 0.1 | 0.2 | — | — |
| Fatty Alcohol | CETYL ALCOHOL | 1.5 | 1.5 | 1.5 | 1.5 |
| Cationic Surfactant | STEARAMIDOPROPYL DIMETHYLAMINE | 0.6 | 0.3 | 1.2 | 1.2 |
| | BEHENTRIMONIUM CHLORIDE | 0.6 | 0.9 | — | — |
| Fatty Carbonate Ester | DICAPRYLYL CARBONATE | 0.9 | 0.9 | 0.9 | 0.5 |
| Dialkyl ether | DICAPRYLYL ETHER | 0.5 | 0.5 | 0.5 | 0.5 |
| Isopropyl ester | ISOPROPYL MYRISTATE | 0.5 | 0.5 | — | — |
| Alkanes | UNDECANE and TRIDECANE | — | — | 0.5 | 0.5 |
| Misc. | ONE OR MORE OF PRESERVATIVES, FRAGRANCE, SALTS, pH ADJUSTERS, NONIONIC SURFACTANTS, ETC. | ≤2 | ≤2 | ≤2 | ≤2 |
| | WATER | 0.024 | 0.036 | — | — |
| | RATIOS | | | | |
| | fatty carbonate ester: dialkyl ether | 1.8 | 1.8 | 1.8 | 1 |
| | fatty alcohol: cationic surfactant | 1.25 | 1.25 | 1.25 | 1.25 |
| | glycol: monoalcohol | 3.7 | 3.7 | 3.7 | 3.7 |
| | fatty carbonate ester: dialkyl ether: alkane(s) | — | — | 1.8:1:1 | 0.5:0.5:0.5 |

The invention compositions of the present disclosure were found to remain clear within a broad range of temperatures such as from room temperature to about 6° C. or less than 6° C.

Example 4

Comparative Compositions

| | | COMPARATIVE FORMULAS | | |
|---|---|---|---|---|
| | INGREDIENT INCI US NAME | O wt. % | P wt. % | Q wt. % |
| Glycol | PROPYLENE GLYCOL | 70-QS 100 | 70-QS 100 | 70-QS 100 |
| Monoalcohol | ETHANOL | 10-20 | 10-20 | 10-20 |
| | ISOPROPYL ALCOHOL | 0.14 | — | 0.14 |
| Fatty Alcohol | MYRISTYL ALCOHOL AND/OR CETYL ALCOHOL | 1-2 | 1-2 | 1-2 |
| Cationic Surfactant | STEARAMIDOPROPYL DIMETHYLAMINE AND/OR BEHENTRIMONIUM CHLORIDE AND/OR CETRIMONIUM CHLORIDE | 1-1.5 | 1-1.5 | 1-1.5 |
| Fatty Carbonate Ester | DICAPRYLYL CARBONATE | 0.9 | 0.9 | 0.9 |
| Dialkyl ether | DICAPRYLYL ETHER | — | — | — |
| Misc. | ONE OR MORE OF PRESERVATIVES, FRAGRANCE, SALTS, pH ADJUSTERS, NONIONIC SURFACTANTS, CATIONIC POLYMERS, ETC. | ≤2 | ≤2 | ≤2 |
| ratio | | | | |
| fatty carbonate ester: dialkyl ether | | 0.9:0 | 0.9:0 | 0.9:0 |
| fatty alcohol: cationic surfactant | | 2-0.7 | 2-0.7 | 2-0.7 |
| glycol: monoalcohol | | 8-3.5 | 8-3.5 | 8-3.5 |

Example 5

Comparative Composition

| | INGREDIENTS INCI US NAME | Comparative Formula R wt. % |
|---|---|---|
| Glycols | GLYCERIN | 1.0 |
| Monoalcohol | ISOPROPYL ALCOHOL | 0.7 |
| Fatty alcohol | CETEARYL ALCOHOL | 7.0 |
| Cationic surfactants | BEHENTRIMONIUM CHLORIDE/ CETRIMONIUM CHLORIDE | 3 |
| Fatty compounds | CETYL ESTERS, WAX, PLANT OIL(S) | 3 to 5 |
| Silicones | AMODIMETHICONE | 2.3 |
| Thickening Agents | XANTHAN GUM/ GUAR DERIVATIVE | 0.2 |
| Misc. | ONE OR MORE OF PRESERVATIVES, FRAGRANCE, SALTS, pH ADJUSTERS, NONIONIC SURFACTANTS, HYDROLYZED PROTEIN, PLANT EXTRACTS, ETC. | ≤2 |
| | WATER | 78 to QS 100 |

Example 6

Comparative Composition

| | INGREDIENTS INCI US NAME | Comparative Formula S wt. % |
|---|---|---|
| Glycols | | — |
| Fatty alcohol | CETEARYL ALCOHOL | 6.0-7.0 |
| Cationic surfactants | BEHENTRIMONIUM CHLORIDE/CETRIMONIUM CHLORIDE | 2.0 |
| Fatty compounds | CETYL ESTERS | 1.0 |
| | SILICONES | 0.5-1.0 |
| Misc. | ONE OR MORE OF PRESERVATIVES, FRAGRANCE, SALTS, pH ADJUSTERS, NONIONIC SURFACTANTS, HYDROLYZED PROTEIN, PLANT EXTRACTS, MONOALCOHOL, VITAMINS, ETC. | ≤2 |
| | WATER | 87.0 TO QS 100 |

Example 7

Hair Evaluation

Example 7A Sensorial Effect on Hair Swatches

The sensorial effect of invention formulas A and B on hair swatches was evaluated and compared to the sensorial effect of comparative formula P.

Two-grams of platinum bleached hair swatches were first washed with a conventional sulfate-based shampoo and rinsed off with water. The swatches were then treated with invention formulas by massaging 0.8 grams of product onto each hair swatch for 30 seconds. The swatches were then rinsed with water for 30 seconds and then allowed to air dry.

The dry treated swatches were evaluated by five experts for sensory feel. Four out of the five experts selected invention formulas A and B as providing a better sensorial effect of smooth feel on the treated hair as compared to comparative formula P.

Example 7B Salon Screening in Hair

An invention formula from Example 1 and a comparative formula X based on the invention formula but not containing dicaprylyl ether and made up to 100 wt. % with propylene glycol were used to treat the hair of human volunteers (N=3) in a salon, the hair of a length from medium to long, with loose curls, fine to medium diameter, and chemically damaged. The professional salon hair dressers evaluated the treated hair and found that the attributes of overall cosmeticity, care, and manageability such as, —detangling, combing, smoothness, conditioning feel, shape, discipline, and sealed ends were found to be noticeably better on the hair treated with the invention formula than on the hair treated with comparative formula X.

Example 7C Salon Screening in Hair

In a salon test, the hair of human volunteers (N=2) of a length from medium to long, with loose curls, fine to coarse diameter, and chemically damaged were first shampooed and rinsed. An invention formula from Example 1 and a comparative formula R were then used to treat the hair. The professional salon hair dressers evaluated the treated hair and found that the attributes of detangling, combing, smoothness, conditioning feel were found to be better on the hair treated with the invention formula than on the hair treated with comparative formula R during rinsing, while the hair was still wet and when the hair was dry.

Example 7D Salon Screening in Hair

In a salon test, the hair of human volunteers (N=6) (chemically damaged) were first shampooed and rinsed. An invention formula from Example 1 and comparative formula X were used to treat the hair of human volunteers (N=6) with chemically damaged hair in a salon. The professional salon hair dressers evaluated the treated hair and found that the attributes of care performances during application, rinse, and on wet and dry hair, visual smoothness and shine were found to be better on the hair treated with the invention formula than on the hair treated with comparative formula X.

Example 7E Salon Screening in Hair

In a salon test, the hair of human volunteers (N=2) of a length from medium to long, with loose curls, fine to coarse diameter, and chemically damaged were first shampooed and rinsed. An invention formula from Example 1 and a comparative formula S were then used to treat the hair. The professional salon hair dressers evaluated the treated hair and found that the attributes of smoothness, and conditioning feel were found to be noticeably better on the hair treated with the invention formula than on the hair treated with comparative formula S.

The terms "comprising," "having," and "including" are used in their open, non-limiting sense.

The terms "a" and "the" are understood to encompass the plural as well as the singular.

The compositions and methods of the present disclosure can comprise, consist of, or consist essentially of the essential elements and limitations of the disclosure described herein, as well as any additional or optional ingredients, components, or limitations described herein or otherwise useful.

The compositions described throughout this disclosure may be a "leave-on" product. A "leave-on" (also called leave-in) product refers to a hair treatment composition that is applied to hair and is not subjected to immediate rinsing and/or washing for at least 4 hours or for a period of time ranging from 4 hours up to 72 hours, from 4 hours up to 48 hours, or from 8 hours up to 36 hours, or from 8 hours up to 24 hours. In other words, the product is applied to the hair and remains on the hair, as styled, i.e., it is not removed from the hair prior to styling the hair.

All percentages, parts and ratios herein are based upon the total weight of the compositions of the present disclosure, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions are to be understood as being modified in all instances by the term "about," meaning within +/−5% of the indicated number.

As used herein, the expression "at least one" is interchangeable with the expression "one or more" and thus includes individual components as well as mixtures/combinations.

The term "active material" as used herein with respect to the percent amount of an ingredient or raw material, refers to 100% activity of the ingredient or raw material.

"Cosmetically acceptable" means that the item in question is compatible with a keratinous substrate such as skin and hair. For example, a "cosmetically acceptable carrier" means a carrier that is compatible with a keratinous substrate such as skin and hair.

The term "hair care" is interchangeable with the term "hair treatment" for purposes of the instant disclosure.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counter-ion. This list of counter-ions, however, is non-limiting.

The expression "inclusive" for a range of concentrations means that the limits of the range are included in the defined interval.

"Volatile", as used herein, means having a flash point of less than about 100° C.

"Non-volatile", as used herein, means having a flash point of greater than about 100° C.

The term "polymers," as defined herein, include homopolymers and copolymers formed from at least two different types of monomers.

The term "INCI" is an abbreviation of International Nomenclature of Cosmetic Ingredients, which is a system of names provided by the International Nomenclature Committee of the Personal Care Products Council to describe personal care ingredients.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

All components and elements positively set forth in this disclosure can be negatively excluded from the claims. In other words, the compositions (nanoemulsions) of the instant disclosure can be free or essentially free of all components and elements positively recited throughout the instant disclosure.

Some of the various categories of components identified may overlap. In such cases where overlap may exist and the composition includes both components (or the composition includes more than two components that overlap), an overlapping compound does not represent more than one component. For example, a fatty acid may be characterized as both a nonionic surfactant and a fatty compound. If a particular composition includes both a nonionic surfactant and a fatty compound, a single fatty acid will serve as only the nonionic surfactant or as only the fatty compound (the single fatty acid does not serve as both the nonionic surfactant and the fatty compound).

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A hair care composition comprising:
   (a) about 20 wt. % or higher of one or more polyols;
   (b) about 5 to about 70 wt. % of one or more monoalcohols having from 2 to 6 carbon atoms;
   (c) about 2 wt. % or less of one or more fatty alcohols selected from cetyl alcohol and myristyl alcohol;
   (d) about 0.1 to about 5 wt. % of one or more cationic surfactants;
   (e) about 1 wt % or less of one or more fatty carbonate esters;
   (f) about 1 wt % or less of one or more dialkyl ethers; and
   (g) 0 wt. % to about 10 wt. % of water;
      wherein all percentages by weight are based on the total weight of the composition; and wherein the composition is a transparent and non-emulsified composition until applied to wet or damp hair or placed in contact with extraneous water, whereupon the composition forms an opaque emulsion.

2. The composition of claim 1, wherein the weight ratio of the polyol(s) to the monoalcohol(s) (polyol(s):monoalcohol(s)) is from about 20:1 to about 1:1.

3. The composition of claim 1, comprising about 20 to about 95 wt. % of one or more polyols, based on the total weight of the composition.

4. The composition of claim 1, wherein the one or more polyols is selected from ethylene glycol, propylene glycol, butylene glycol, hexylene glycol, pentylene glycol, diethylene glycol, dipropylene glycol, 1,3 propanediol, glycerin, and mixtures thereof.

5. The composition of claim 1, wherein the one or more polyols includes propylene glycol.

6. The composition of claim 1, wherein the one or more monoalcohols is selected from ethanol, butanol, pentanol, hexanol, isopropyl alcohol, cycohexanol, isobutyl alcohol, 2-methyl-2-butanol (2-methylbutan-2-ol), and a mixture thereof.

7. The composition of claim 1, wherein the one or more polyols includes propylene glycol and the one or more monoalcohols includes ethanol.

8. The composition of claim 7, wherein the weight ratio of propylene glycol to ethanol (propylene glycol:ethanol) is from about 15:1 to about 1:1.

9. The composition of claim 1, comprising from about 0.1 to about 2 wt. % of the one or more fatty alcohols, based on the total weight of the composition.

10. The composition of claim 1, wherein the one or more cationic surfactants are selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof.

11. The composition of claim 1, wherein the weight ratio of the one or more fatty alcohols to the one or more cationic surfactant (fatty alcohol(s):cationic surfactant(s)) is from about 2:1 to about 1:1.

12. The composition of claim 1, wherein the one or more fatty carbonate esters is selected from dialkyl carbonates.

13. The composition of claim 1, wherein the one or more fatty carbonate esters is selected from C14-15 dialkyl carbonate, dicaprylyl carbonate, diethyl carbonate, dihexyl carbonate, diethylhexyl carbonate, dimethoxyphenyl phenyloxoethyl ethylcarbonate, dimethyl carbonate, dipropyl carbonate, dipropylheptyl carbonate, dioctyl carbonate, and a mixture thereof.

14. The composition of claim 1, wherein the one or more fatty carbonate esters includes dicaprylyl carbonate.

15. The composition of claim 1, wherein the one or more diakyl ether is selected from dicaprylyl ether, dicetyl ether, dodecyl ether, dilauryl ether, dimyristyl ether, distearyl ether, diisononyl ether, and a mixture thereof.

16. The composition of claim 1, wherein the one or more diakyl ether includes dicaprylyl ether.

17. The composition of claim 1, wherein the weight ratio of the one or more fatty carbonate esters to the one or more dialkyl ethers (fatty carbonate ester(s): dialkyl ether(s)) is from about 2:1 to 1:1.

18. The composition of claim 1, wherein the composition further comprises about 0.1 to about 2 wt. % of one or more isopropyl esters, based on the total weight of the composition.

19. The composition of claim 18, wherein the composition further comprises one or more additional esters other than isopropyl esters selected from glycerol fatty esters, sucrose fatty esters, sorbitan fatty ester, fatty acid esters, and mixtures thereof.

20. The composition of claim 1, wherein the composition further comprises about 0.1 to about 10 wt. %, based on the total weight of the composition, of one or more alkanes selected from undecane, tridecane, and a mixture thereof.

21. The composition of claim 1, wherein the composition further comprises about 0.1 to about 20 wt. % of one or more thickening agents.

22. The composition of claim 1, wherein the composition further comprises:
about 0.1 to about 20 wt. %, based on the total weight of the composition, of one or more thickening agents selected from polyacrylate crosspolymers or crosslinked polyacrylate polymers, cationic acrylate copolymers, anionic acrylic or carboxylic acid polymers, polyacrylamide polymers, polysaccharides, gums, polyquaterniums, vinylpyrrolidone homopolymers/copolymers, C8-24 hydroxyl substituted aliphatic acid, C8-24 conjugated aliphatic acid, sugar fatty esters, polyglyceryl esters, and a mixture thereof.

23. The composition of claim 1, wherein the composition has a viscosity of about 10 mPa·s to about 10,000 mPa·s at 25° C., prior to application to the wet or damp hair or to being placed in contact with extraneous water.

24. The composition of claim 1, wherein the composition is essentially free of silicones.

25. The composition of claim 1, wherein the composition is essentially free of butylene glycol.

26. A hair care composition comprising:
(a) about 30 to about 85 wt. % of one or more polyols;
(b) about 5 to about 50 wt. % of one or more monoalcohols having from 2 to 6 carbon atoms;
 wherein the weight ratio of the polyol(s) to monoalcohol(s) (polyol(s):monoalcohol(s)) is from about 10:1 to about 1.5:1;
(c) about 2 wt. % or less of one or more fatty alcohols selected from cetyl alcohol and myristyl alcohol;
(d) about 0.1 to about 5 wt. % of one or more cationic surfactants;
 wherein the weight ratio of the one or more fatty alcohols to the one or more cationic surfactant (fatty alcohol(s):cationic surfactant(s)) is from about 2:1 to about 1.5:1;
(e) about 1 wt % or less of one or more fatty carbonate esters;
(f) about 1 wt % or less of one or more dialkyl ethers; and
(g) 0 wt. % to about 10 wt. % of water;
 wherein the weight ratio of the one or more fatty carbonate esters to the one of more dialkyl ethers (fatty carbonate ester(s):dialkyl ether(s)) is from about 2:1 to 1.6:1;
wherein the composition is a transparent and non-emulsified composition until applied to wet or damp hair or placed in contact with extraneous water, whereupon the composition forms an opaque emulsion having a lamellar phase; and
wherein all percentages by weight are based on the total weight of the composition.

27. The composition of claim 26, wherein the one or more polyols is selected from ethylene glycol, propylene glycol, butylene glycol, hexylene glycol, pentylene glycol, 1,3-propanediol, diethylene glycol, dipropylene glycol, caprylyl glycol, glycerin, and a mixture thereof.

28. The composition of claim 26 comprising:
about 50 to about 80 wt. % of propylene glycol;
about 5 to about 30 wt. % of ethanol;
one or more cationic surfactants selected from cetrimonium chloride, behentrimonium chloride, behentrimonium methosulfate, stearamidopropyl dimethylamine, and a mixture thereof;
one or more fatty carbonate esters selected from dialkyl carbonates; and
one or more dialkyl ethers including dicaprylyl ether.

29. The composition of claim 26, wherein the composition has a viscosity of about 10 mPa·s to about 5,000 mPa·s at 25° C., prior to application to the wet or damp hair.

30. A method for treating hair comprising applying a hair care composition to wet or damp hair or placing the composition in contact with extraneous water for application to the hair, the composition comprising:
(a) about 20 wt. % or higher of one or more polyols;
(b) about 5 to about 70 wt. % of one or more monoalcohols having from 2 to 6 carbon atoms;
(c) about 2 wt. % or less of one or more fatty alcohols selected from cetyl alcohol and myristyl alcohol;
(d) about 0.1 to about 5 wt. % of one or more cationic surfactants;
(e) about 1 wt % or less of one or more fatty carbonate esters;
(f) about 1 wt % or less of one or more dialkyl ethers;
 wherein the composition is a transparent and non-emulsified composition until applied to the wet or damp hair or placed in contact with extraneous water, whereupon the composition forms an opaque emulsion; and
wherein all percentages by weight are based on the total weight of the composition.

31. The method of claim 30, wherein the composition has a viscosity of about 10 mPa·s to about 5,000 mPa·s at 25° C., prior to application to the wet or damp hair.

32. The method of claim 30, wherein the weight ratio of the polyol(s) to the monoalcohols (polyol(s):monoalcohol(s)) is from about 20:1 to about 1:1.

33. The method of claim 30, wherein:
the hair is not rinsed with water after application of the composition; or
the hair is rinsed with water after application of the composition.

34. The method of claim 30, wherein the method:
conditions the hair; and/or
provides curl definition to the hair; and/or
provides frizz control to the hair; and/or
improves ease of compatibility and detangling of hair; and/or
protects the hair from damage; and/or
increases or imparts shine on hair; and/or
increases the appearance of hair volume.

* * * * *